United States Patent [19]

Schröder

[11] 4,246,900
[45] Jan. 27, 1981

[54] DIAPER INCLUDING MOISTURE-RESPONSIVE SEAL MEANS

[75] Inventor: Friedrich-Wilhelm Schröder, Heidenheim, Fed. Rep. of Germany

[73] Assignee: Paul Hartmann Aktiengesellschaft, Heidenheim, Fed. Rep. of Germany

[21] Appl. No.: 19,138

[22] Filed: Mar. 9, 1979

[30] Foreign Application Priority Data

Mar. 11, 1978 [DE] Fed. Rep. of Germany ....... 2810680

[51] Int. Cl.³ .............................................. A41B 13/02
[52] U.S. Cl. ................................................... 128/287
[58] Field of Search ........................ 128/284, 286, 287

[56] References Cited

U.S. PATENT DOCUMENTS

| | | | |
|---|---|---|---|
| 3,417,751 | 12/1968 | Murdoch | 128/284 |
| 3,488,778 | 1/1970 | Goujon et al. | 728/284 |
| 3,860,003 | 1/1975 | Buell | 128/287 |
| 4,029,100 | 6/1977 | Karami | 128/284 |

*Primary Examiner*—C. Fred Rosenbaum
*Attorney, Agent, or Firm*—Laubscher & Laubscher

[57] ABSTRACT

A diaper construction is disclosed including a pair of elastic leg seal members extending longitudinally of the diaper adjacent each side edge thereof, the leg seal members being operable between expanded and contracted conditions, respectively, and moisture-responsive devices initially maintaining the leg seal members in their expanded conditions, whereby when the diaper is worn by a user and the leg seal members become moisturized, the moisture-responsive devices are operable to release the leg seal members, whereby the leg seal members contract into sealing engagement with the user's leg.

8 Claims, 4 Drawing Figures

DIAPER INCLUDING MOISTURE-RESPONSIVE SEAL MEANS

BRIEF DESCRIPTION OF THE PRIOR ART

This invention relates to a panty diaper with a moisture-impermeable outer layer, an absorbent body arranged thereupon, and an inside lining which covers this body, which is connected along the edges with the outer layer, and which is moisture permeable, as well as contractable leg seal means arranged in the area of the edges of the diaper that abut the user's legs, respectively.

Panty diapers of this kind are normally discarded after they have been used once. They are suitable above all for absorbing the excretions of an infant of diaper age, but they can also be used for absorbing or intercepting the excretions of patients of any age. This kind of panty diaper can be worn while lying in bed and while walking, standing, or sitting. The suction body of the panty diaper catches the excretions and stores them so that the bedding or the underwear will not be dirtied.

A panty diaper is known with an elastic layer or insert in the area of the edge of the leg seal (German Offenlegungschrift No. 24 54 590), where elastically contractable bands are applied, in a stretched state, to the longitudinal outer parts of the panty diapers. In the relaxed state, the bands contract and place the side edges of the panty diapers, in the area of the leg seal, essentially moisture-proofed against the leg circumference in the pace or step area. One advantage of these panty diapers consists in the fact that, because of the elastic contraction of the bands at all times, in which condition the panty diaper is worn, there is a more or less severe constriction of the shank which can lead to blood circulation disorders and skin irritations.

It is not necessary either to have the edge area of the panty diaper rest elastically against the shank in such a manner when the infant or the patient will not eliminate any liquid excretions. Furthermore, the elastic sealing in the area of the edge of the leg seal is not necessary when the excreted liquid volume is so dimensioned that it will be fully compensated by the absorption capacity of the absorbent body. Indeed, an elastic leg seal and thus, so th speak, a "sealing sleeve or cuff" will be necessary only when the absorbent capacity of the absorbent body has been exceeded and when there is a possibility that excretions might come out of the absorbent body in the area of the leg seal and might contaminate the bedding or the underwear.

SUMMARY OF THE INVENTION

It is the primary object of the present invention to provide a panty diaper whose sealing leg seal will go into action only in response to heavy liquid development.

According to the invention, this problem is solved by providing in the edge area of the leg seal a flexible band which is inelastic in the dry state, but which can be placed into an elastic state by wetting with liquid media. The layer is preferably maintained its expanded condition by means of water-soluble substances.

BRIEF DESCRIPTION OF THE DRAWING

Other objects and advantages of the invention will become apparent from a study of the following specification, when viewed in the light of the accompanying drawing, in which.

DETAILED DESCRIPTION

Figure 1:
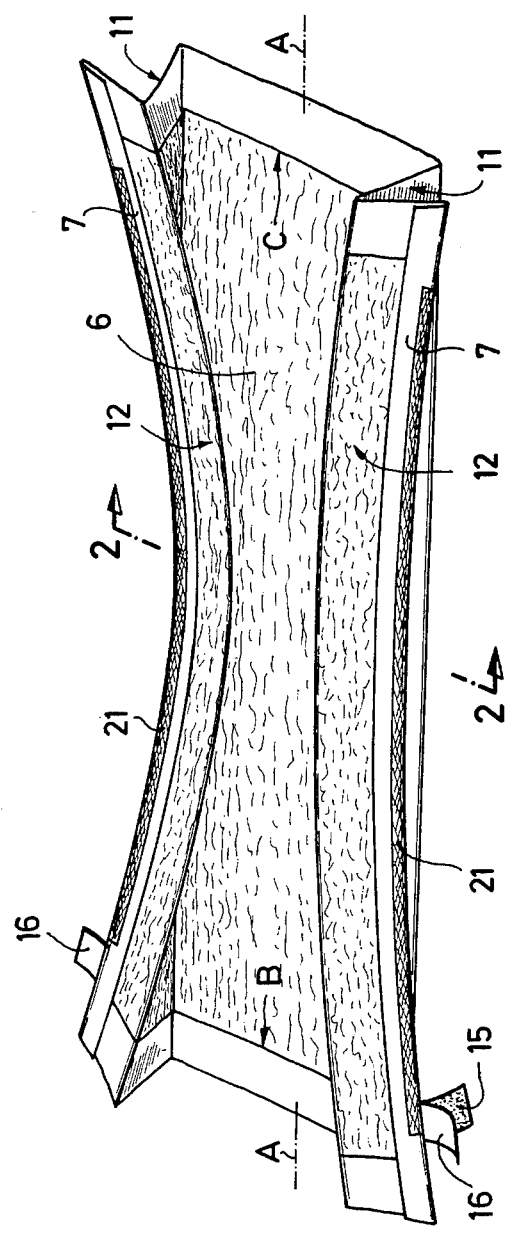
FIG. 1 is a perspective view of a first diaper embodiment in accordance with the present invention.
Figure 2:
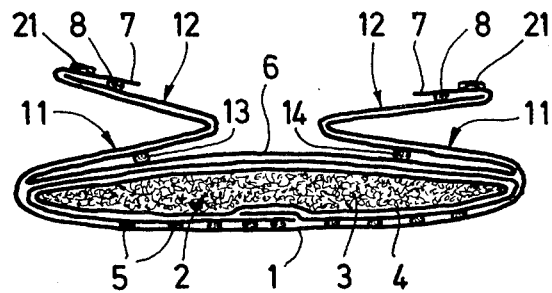
FIG. 2 is a sectional view taken along line 2—2 of FIG. 1.

The panty diapers illustrated in FIGS. 1 and 2 include a rectangular, moisture-impermeable outer layer 1, which, for example, can consist of polyvinylchloride, polyethylene, or other synthetic plastic substance on which is arranged, symmetrically with respect to the longitudinal center axis A, an absorbent body 2 consisting of a resilient, absorbent cellulose particle layer 3. Instead of cellulose particles, several moisture-absorbing paper or cellulose fiber layers may be piled on top of each other to make up the absorbent body 2. The layer 3, which forms the absorbent body 2, is enclosed by a thin, moisture-permeable, absorbent paper layer 4 made of tissue cellulose. To make layer 4, other skin-safe, liquid-permeable materials are also suitable. Layer 4 need enclose absorbent body 3 only partly or can be omitted entirely. Layer 4 preferably has the task of distributing the liquid as uniformly as possible over the absorbent body. Absorbent body 2, which in the longitudinal direction is somewhat shorter than the panty diaper and which in each case extends roughly to the lines labeled B and C, respectively, in FIG. 1 is adhesively secured by layer 4 upon the inside of the outer layer 1, thereby to prevent the body from being shifted. The points of adhesion 5 between layer 4 and outer layer 1 are indicated in FIG. 2.

Adjacent the body side of a child to be diapered, the outer layer 1 and the absorbent body 2 are covered by an inside coating 6 formed of a moisture-permeable fleece-like substance or material, which coating layer 6 possesses textile properties, that is to say, it is soft and drapable and does not form any sharp crumpling folds. The layer 6 preferably consists of viscose fibers. In the version of a panty diaper illustrated in FIGS. 1 and 2, the inside layer 6 is connected, along the lateral edges of the diaper, that is to say, roughly in the area between the outer lateral edges and lines B and D (FIG. 1), with the outer layer 1. This connection can be accomplished by an adhesive, or, if the inside layer 6 consists of sealable material, it can be done by heat sealing. Along the outer side edges of the panty diaper, running parallel to the longitudinal center axis A, outer layer 1 overlaps the inside coating or layer 6 with a cover or flap 7. In the area of this flap, inside layer 6 and outer layer 1 are connected with each other, for example, they are adhesively connected, something which is indicated in FIG. 2 by means of adhesive points 8.

In the version of the invention illustrated in FIGS. 1 and 2, the outer layer 1 and the inside layer 6 are folded, in the longitudinal direction, in dove-tail fashion, toward the center axis A, so that the diaper portions 11 and 12, located on both sides of the center axis, will form a so-called "vault fold". In the crotch area of the diapers, that is to say, in the area which, when the diaper is used, comes to rest between the shanks of the child, the diaper portions 11, which happen to be on the inside, are connected with the inside layer 6, resting above or on top of the absorbent body 2, along places 13,14 (FIG. 2) which are located symmetrically with respect to the longitudinal center axis A. As a result, the diaper is on the whole made narrower as it comes to be used in the crotch area and it cannot be folded as far apart there as it can along its two outer lateral edges.

Figure 3:
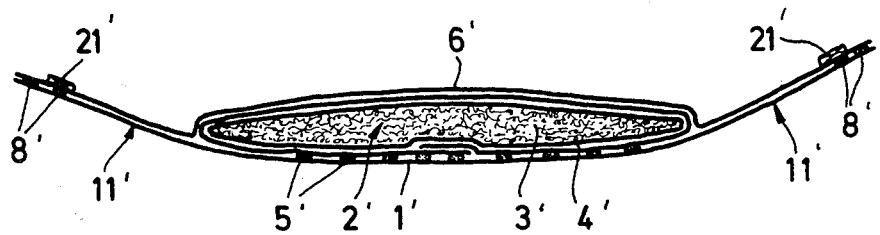
FIG. 3 is a sectional view of a second embodiment of the invention.

FIG. 3 shows another version of the invention where reciprocally corresponding parts have been labeled with the same reference symbols. In contrast to FIG. 2, the outer layer 1' and the inside layer 6', in the version according to FIG. 3, are not folded in, in dove-tail fashion. Absorbent body 2' can extend more or less widely over the width of the panty diaper and in another version of the invention it can also participate in the "vault fold" according to FIG. 2. In FIG. 3, furthermore, outer layer 1' is not folded over the outer edge of inside lining or layer 6', so that in this version, the flap or envelope 7 of FIG. 2 is omitted.

Figure 4:
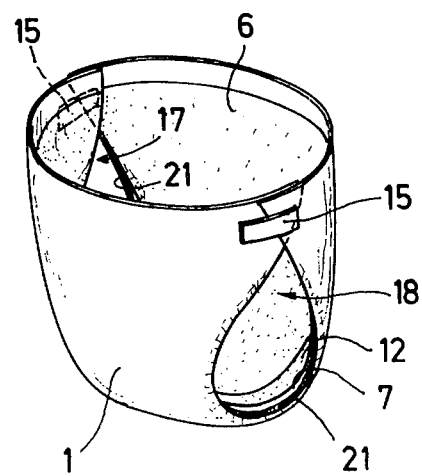
FIG. 4 illustrates the configuration of the diaper as it is being worn by a user.

Adhesive strips 15, with removable protective sheet 16, are arranged along the panty diaper, see FIG. 1. After removal of the protective sheet, the diaper is closed in the known manner, like a panty, after having been applied against the body of a child or patient. This is the form in which the panty diaper is illustrated in FIG. 4. The edge areas of the leg seals, which result in this process, have been labeled 17 and 18, respectively.

As an essential element of the invention, contractable bands 21 are attached on the inside or the topside of the panty diaper in the area of the edge of the leg seal. In the version according to FIGS. 1 and 2, these bands 21 are fastened on the topside of the flaps 7, whereas in the version according to FIG. 3, they are fastened on the topside of the inside layer 6. As shown in FIG. 1, bands 21 do not extend over the entire length of the panty diaper. The bands 21 can border directly on the lateral outer edge of the panty diaper (FIGS. 1 and 2), or they can be arranged at a certain interval from that edge (FIG. 3). In the versions illustrated, the band 21 is in each case fastened as "coating or layer" directly on the topside of the panty diaper. In other versions, the band 21, for example, can also be inserted between two layers of diapers, for example, the outer foil 1 and the inside layer 6, and it can be fastened there.

Band 21 consists of a material which is inherently elastic, that is to say, it contracts again after having been stretched. According to the characterizing feature of the invention, prior to the arrangement of band 21 on the panty diaper, it is so treated in the stretched state according to the invention that it remains flexible but that it will no longer contract. Thus, the stretched band is here treated by means of water-soluble substances which maintain the band in the stretched condition. When the liquid components retained in the absorbent body 2, reach the outer edge area of the panty diaper, those substances which stabilize bands 21 in the stretched state are dissolved, whereupon the elastic properties of band 21 now again go into action and trigger a contraction in the edge areas 17,18 of the panty diaper. As a result of this contraction, there developes a liquid-proof leg seal in the area of the shank. This attains the objective of causing the leg seal to come to rest against the shank in an elastically sealing manner only when this really becomes necessary due to heavy liquid development.

In general, the above mentioned adjustment of band 21 in the stretched, noncontractable state, can be achieved in that an in itself elastic band is covered and soaked, in the stretched state, with a gelatinous or viscous mass, whereupon we remove the solvent of this mass or let it evaporate, so that the originally fluid mass will still become rigid and, as a result, the in itself elastic band, which has a contraction tendency, will be fixed or stabilized in the stretched state. The mass here is to become so rigidified that the band will remain flexible and so that it will not hinder the application of the dry diaper. In this way, the originally fluid mass, when in the dry state, prevents the contraction of the band. Because the gelatinous or viscous mass consists of a substance which, due to wetting with watery media, regains its fluid consistency and is dissolved, the stretched, elastic band 21 regains its mobility or flexibility and will withdraw into its more or less relaxed initial position.

Band 21 is preferably made of an elastic fabric which, for example, contains rubber threads, and elastic mesh, for example, a weft, a double-rib loom fabric, or some other kind of textile or textile-like material, for example, a fleece material, whereby one merely needs to make certain that the band will be elastically deformable at least in the longitudinal direction, in other words, in the direction of its largest geometric extent. The production of band 21 from elastic textile material will facilitate impregnation with the above-mentioned gelatinous or viscous mass. The elastic band can also be made up of a compact, for example, foil-like or thread-like (single-thread) material with longitudinally elastic properties. Here we consider rubber, elastomeric materials, open-pore and closed-pore elastic foam in the form of rubber sponge, sponge rubber, foam rubber, or the like.

To maintain band 21 in the stretched, flexible state, there may be used suitable natural substances, such as gelatins, glues, alginic acid, starch; chemically altered natural substances, such as compounds derived from alginic acid, especially its salts, cellulose, for example, cellulose ether or cellulose ester, or compounds derived from starch; synthetic chemical compounds with the property of being fluid, in contact with solvents, especially water, and becoming flexibly rigidified after withdrawal of solvent, and again becoming fluid after the addition of watery media, for example, polyvinylalcohol and polyvinylpyrrolidon or other synthetic substances, such as water-soluble acrylic resins, polyester resins, and the like.

Band 21, which is maintained in the stretched condition, is fastened inseparately or indissolubly in the edge area of leg seal 17,18 on the panty diaper. The fastening is preferably accomplished, for example, by means of a water-insoluble adhesive, or by means of sewing, stapling, or the like. When an adhesive is used, it must engage directly on the basic material of band 21 and not just on the water-soluble, gelatinuous or viscous mass, because, if that were the case, the band would become separated from the panty diaper when this mass is dissolved. It was found that a material, soaked with a gelatinous or viscous mass of the above kind and thus rigidified, can be inseparably glued together with one of the layers in the panty diaper. One can also coat an elastic "monofile" or "single-thread" core material only on one side with the gelatinous or viscous mass and one can glue it on the other, uncoated side, together with the panty diaper.

If bands 21, as illustrated in FIGS. 1 and 2, are arranged along the panty diapers in such a manner that they are freely exposed toward the top, then they will come to rest directly against the body surface and bring about a particularly tight seal. The length of bands 21 in this case is so dimensioned that the entire leg circumference will be enclosed by the bands. In the illustration in FIG. 4, assume that the absorption capacity of the absorbent body 2 has been exceeded and that liquid is threatening to leak out of the absorbent body, sideways, in the leg area. In that case, the previously-mentioned fixation—brought about, for example, by the gelatinous mass—of the elastic band 21, which is stiffened in the stretched state but which is still in itself elastic, is separated or dissolved, as a result of which band 21 and the area of the panty diaper connected with it will contract. That produces the liquid-proof leg seal.

Another advantage of the invention consists in the simplified manufacture of panty diapers with elastic leg seal. Until now elastic bands or the like at first had to be stretched by mechanical means and had to be connected with the diaper in this state, after which the mechanical means could be removed; but now such mechanical means can be eliminated in making a panty diaper according to the invention because the stretched band 21 is in itself fixed by means of the gelatinous or viscous mass. Furthermore, bands 21, which in the dry state are flexible but not elastic, advantageously result in a neatly folded panty diaper. If bands 21 were in the elastically contracted state along the dry panty diaper, the latter could not be smoothly stacked and packaged because of the resultant folds.

While the preferred forms and embodiments of the invention have been illustrated and described, it will become apparent that changes may be made without deviating from the invention set forth above.

What is claimed is:
1. A diaper construction, comprising
   (a) a horizontal generally rectangular outer layer (1) formed of moisture-impermeable material;
   (b) a moisture-permeable generally rectangular inner liner layer (6) arranged above, and connected at its edges with, said outer layer;
   (c) a pair of elastic flexible leg seal members (21) connected with the upper surface of one of said layers and extending longitudinally adjacent the longitudinal edges thereof, respectively, said leg seal members being elastically operable between expanded and contracted conditions, respectively; and
   (d) moisture-responsive means temporarily maintaining said leg seal members in their expanded conditions, whereby when the diaper is mounted on a user and the leg seal members become moisturized, said moisture-responsive means is operable to release said leg seal members for contraction into sealing engagement with the user's legs, respectively.
2. A diaper as defined in claim 1, wherein said moisture-responsive means comprises a water-soluble coating arranged on each of said leg seal members, respectively.
3. A diaper as defined in claim 2, wherein said leg seal means extend generally parallel with the leg sealing portions (17, 18) of the diaper, respectively.
4. A diaper as defined in claim 3, wherein said leg seal means is arranged in the inside of the diaper.
5. A diaper as defined in claim 4, wherein the length of each of said leg seal means is less than that of the leg sealing portions of the diaper.
6. A diaper as defined in claim 1, wherein the leg seal member is formed from a synthetic high-molecular chemical compound.
7. A diaper as defined in claim 1, wherein each of said leg seal members includes a textile-like flat surface.
8. A diaper as defined in claim 1, wherein said moisture-response means is selected from the group consisting of gelatin, starch, alginic acid, cellulose esters, cellulose ethers, starch derivatives, and derivatives of polyvinylalcohol and polyvinylpyrrolidon.

* * * * *